United States Patent [19]

Maxfield Wilson et al.

[11] Patent Number: 5,780,319

[45] Date of Patent: Jul. 14, 1998

[54] IMMUNOASSAYS TO DETECT ANTIPHOSPHOLIPID ANTIBODIES

[75] Inventors: Nancy Maxfield Wilson, Bloomington, Minn.; Catherine Larue, Vaucresson, France

[73] Assignee: Pasteur Sanofi Diagnostics, France

[21] Appl. No.: 636,733

[22] Filed: Apr. 19, 1996

[51] Int. Cl.$^6$ .................................................. G01N 33/543
[52] U.S. Cl. ........................... 436/518; 422/57; 422/58; 435/7.1; 435/7.2; 435/7.8; 435/7.92; 435/7.93; 435/7.94; 435/7.95; 435/287.9; 436/523; 436/534; 436/71; 436/822; 436/823; 436/829
[58] Field of Search ..................... 422/57, 58; 435/7.1, 435/7.2, 7.8, 7.92, 7.93, 7.94, 7.95, 287.9; 436/518, 523, 534, 71, 822, 823, 829

[56] References Cited

U.S. PATENT DOCUMENTS

| | | |
|---|---|---|
| 4,193,983 | 3/1980 | Ullman et al. . |
| 4,235,871 | 11/1980 | Papahadjopoulos et al. . |
| 4,483,929 | 11/1984 | Szoka . |
| 4,485,054 | 11/1984 | Mezei et al. . |
| 4,668,638 | 5/1987 | Janoff et al. . |
| 4,698,299 | 10/1987 | Janoff et al. . |
| 4,707,441 | 11/1987 | Ahmad et al. . |
| 4,713,324 | 12/1987 | Fox et al. . |
| 4,717,676 | 1/1988 | Wagner et al. . |
| 4,762,915 | 8/1988 | Kung et al. . |
| 4,783,400 | 11/1988 | Canova-Davis et al. . |
| 4,839,276 | 6/1989 | Adolfsen et al. . |
| 4,874,710 | 10/1989 | Piran . |
| 4,933,121 | 6/1990 | Law et al. . |
| 4,948,590 | 8/1990 | Hawrot et al. . |
| 5,017,501 | 5/1991 | Wong . |
| 5,094,785 | 3/1992 | Law et al. . |
| 5,106,963 | 4/1992 | Hwang et al. . |
| 5,108,934 | 4/1992 | Rokugawa et al. . |
| 5,248,590 | 9/1993 | Rutner et al. . |
| 5,296,347 | 3/1994 | LaMotte, III . |
| 5,312,730 | 5/1994 | Piran et al. . |
| 5,344,758 | 9/1994 | Krilis et al. . |
| 5,374,715 | 12/1994 | Kanno et al. . |
| 5,399,331 | 3/1995 | Loughrey et al. . |
| 5,494,803 | 2/1996 | Carbonell et al. . |

FOREIGN PATENT DOCUMENTS

| | | |
|---|---|---|
| 0036277 | 3/1981 | European Pat. Off. . |
| 0245926 | 3/1987 | European Pat. Off. . |
| 2 021 262 | 4/1979 | United Kingdom . |
| 8501580 | 4/1985 | WIPO . |
| 9110138 | 7/1991 | WIPO . |
| WO 93/10226 | 5/1993 | WIPO . |
| WO 94/22015 | 9/1994 | WIPO . |

OTHER PUBLICATIONS

Bruce P. Gaber, et al., "Liposome–Based Immunoassays for Detection of Small and Large Molecules," *Adv. Exp. Med. Bio.*, 238, 209–214 (1988).

Rodney J. Y. Ho, et al., "Interactions of Antigen–Sensitized Liposomes with Immobilized Antibody: A Homogeneous Solid–Phase Immunoliposome Assay," *The Journal of Immunology*, vol. 134, No. 6, Jun. 1985, pp. 4035–4040.

Yoshio Ishimori, et al., "Stable Liposomes for Assays of Human Sera," *Clinical Chemistry*, 39/7, 1439–1443 (1993).

Troy D. Jaskowski, et al., "Comparison of Three Commercially Available Enzyme Immunoassays for the Screening of Autoantibodies to Extractable Nuclear Antigens," *Journal of Clinical Laboratory Analysis*, 9:166–172 (1995).

Kari Keinänen, et al., "Biosynthetic Lipid–Tagging of Antibodies," *FEBS Letters*, 346 (1994) 123–126.

Lee D. Lesserman, et al., "Covalent Coupling of Monoclonal Antibodies and Protein A to Liposomes: Specific Interaction with Cells in Vitro and in Vivo," *Liposome Technology*, vol. III Chapt. 2, 29–39 (© 1984, 1992).

H.C. Loughrey, et al., "Optimized Procedures for the Coupling of Proteins to Liposomes," *Journal of Immunological Methods*, 132 (1990) 25–35.

H. Patrick McNeil, et al., "Immunology and Clinical Importance of Antiphospholipid Antibodies," *Advances in Immunology*, vol. 49, 193–280 (© 1991).

Eng M. Tan, "Antinuclear Antibodies: Diagnostic Markers for Autoimmune Diseases and Probes for Cell Biology," *Advances in Immunology*, vol. 44, 93–151 (© 1989).

Edwin F. Ullman, et al., "Use of Liposome Encapsulation in a Combined Single–Liquid Reagent for Homogeneous Enzyme Immunoassay," *Clinical Chemistry*, 33/9, 1579–1584 (1987).

Mamoru Umeda, et al., "Application of Sandwich Method to Determine a Serum Protein Component with Antibody–Bearing Liposomes," *Journal of Immunological Methods*, 95 (1986) 15–21.

Walter L. Binder, "The Anticardiolipin ELISA Test," *American Clin. Lab*, Oct. 1992.

Timothy D. Heath, et al., "The Development and Application of Protein–Liposome Conjugation Techniques," *Chemistry and Physics of Lipids*, 40 (1986) 347–358.

Rodney J. Y. Ho, et al., "Target–Sensitive Immunoliposomes: Preparation and Characterization," *Biochemistry*, 1986, 25, 5500–5506.

(List continued on next page.)

*Primary Examiner*—James C. Housel
*Assistant Examiner*—Bao-Thuy L. Nguyen
*Attorney, Agent, or Firm*—Fredrikson & Byron, P.A.

[57] ABSTRACT

Liposome reagents used in assays to detect the presence or amount of an analyte in a test sample, particularly where the analyte is antiphospholipid antibodies are described. The liposome reagents comprise a liposome, a ligand chosen to bind specifically with the analyte and associated with the liposome membrane, and a haptenated component associated with the membrane of the liposome where the hapten is chosen to bind specifically to a receptor bound to a solid phase or to a label compound that is an element of a signal detection system and where the liposome reagent is prepared so that during the assay the linkage between the solid phase and ligand of the liposome reagent is maintained.

24 Claims, No Drawings

OTHER PUBLICATIONS

Kenji Hosoda, et al., "Homogeneous Immunoassy for $X_2$ Plasmin Inhibitor ($H_2$ PI)and $X-_2$ PI–Plasmin Complex. Application of a Sandwich Liposome Immune Lysis Assay (LILA) Technique," *Journal of Immunological Methods*, 121 (1989) 121–128.

Chong–Kook Kim, et al., "Liposome Immunoassay (LIA) with Antigen–Coupled Liposomes Containing Alkaline Phosphatase," *Journal of Immunological Methods*, 159 (1993) 101–106.

Laurie Locascio–Brown, et al., "Liposome–Based Flow–Injection Immunoassay for Determining Theophylline in Serum," *Clinical Chemistry*, vol. 39, No. 3, 1993 p. 386–391.

R. A. Schwendener, et al., "n–Alkyl–Glucosides as Detergents for the Preparation of Highly Homogeneous Bilayer Liposomes of Variable Sizes (60–240 nm 0) Applying Defined Rates of Detergent Removal by Dialysis," *Biochemical and Biophysical Research Communications*, vol. 100, No. 3, 1055–1062, 1981.

Regan G. Shea, et al., "Synthesis, Hybridization Properties and Antiviral Activity of Lipid–Oligodeoxynucleotide Conjugates," *Nucleic Acids Research*, vol. 18, No. 13, pp. 3777–3783 (© 1990).

Francis Szoka, Jr., et al., "Comparative Properties and Methods of Preparation of Lipid Vesicles (Liposomes)," *Ann. Rev. Biophy, Bioeng.*, 1980 9:467–508.

Package Insert for Diastat Anti–Cardiolipin Kit. (Undated).

Package Insert for Diastat Total Anti–Cardiolipin Kit. (Undated).

Shield Diagnostics Ltd., Diastat Anti–Cardiolipin IgG and IgM Kit for in vitro diagnostic use 96 Test Kit. (Undated).

IMMUNOASSAYS TO DETECT ANTIPHOSPHOLIPID ANTIBODIES

FIELD OF THE INVENTION

The present invention relates to assays using novel liposome reagents having ligand associated or incorporated into the liposome bilayer to facilitate the detection of analyte in a patient sample. In one embodiment, the invention relates to immunoassays using the liposome reagents to detect antibodies to phospholipids such as cardiolipin, or the like.

BACKGROUND OF THE INVENTION

This invention details novel assay formats employing novel liposome reagents in assays to detect analyte in a patient sample. In one embodiment of this invention, lipids are formulated into liposomes that incorporate target ligand to detect analyte in a sample. Often the detection of analytes such as those associated with a particular autoimmune disease is difficult because the concentration of analyte in a patient sample is very low. The use of liposomes having ligand associated with or incorporated into the bilayer permits increased ligand binding capacity of the assay. Where microplate format assays have ligand or analyte bound directly to the solid phase, molecular interactions may be sterically hindered. In the assay format of the invention, the ligand is intercalated into a more fluid gel-type matrix, which may allow substantial steric flexibility. Moreover, assays employing the liposome reagents of the invention may have the advantage of presenting ligand for detection or interaction with the analyte in a more native conformation than in solid phase assays where ligands directly bound to the surface may be structurally altered.

The use of liposomes comprised of phospholipids as reagents in homogeneous immunoassays to detect analytes has been described. These assays employ liposomes to encapsulate reporter molecules. U.S. Pat. No. 5,248,590 to H. Rutner et al. states: "When used in an immunoassay, a liposome generally encapsulates a reporter molecule such as a dye or an enzyme and is complexed with a ligand, usually an antigen or antibody." Examples of these assays are described in U.S. Pat. Nos. 4,193,983 to Ullman, et al., 4,483,929 to Szoka, 4,783,400 to Canova-Davis, et al., 4,874,710 to Piran and 4,668,638 to Janoff, et al. In these assays the liposome may be complexed with ligand either covalently or noncovalently through intercalation with hydrophobic molecules or portions of such molecules into the hydrophobic bilayer. The ligand is usually an antibody or antigen that specifically binds the analyte to be detected in the sample. In the cited examples, when the liposome with associated ligand is contacted with a patient's sample, analyte in the sample complexes with the ligand resulting in lysis of the liposome, typically through a complement-mediated lysis. The amount of reporter molecule released into the aqueous solution is determined and this amount is related to the concentration of the analyte being detected.

Significant problems associated with these reporter-encapsulated immunoassays have been identified. First, liposome based assays that require lysis are susceptible to non-specific lysis either by endogenous complement present in the test sample or by liposome degradation leading to leakage of the reporter molecule from the liposome. Therefore, maintaining the integrity of the liposomes is essential to reporter-encapsulated assay sensitivity and specificity. A second disadvantage of lysis-mediated liposomal detection systems is that when the concentration of a particular analyte in a patient sample is low, the use of more concentrated test sample can result in non-specific liposome lysis due to the presence of endogenous complement, and the like, unless the test sample is pre-treated to remove such components. Sample pre-treatment, however, adds time and costs to any assay. Moreover, the pre-treating agent must be carefully chosen so that analyte present in the sample is not denatured or degraded by the agent and the integrity of the liposome is maintained.

While maintaining many of the advantages of liposome-based assays currently in use as described previously, assays of this invention extend the applicability of such assay design by overcoming deficiencies that limit the utility of the liposome-encapsulated reporter approach. For example, the assays of this invention do not rely on encapsulated reporter. Maintaining integrity of the liposomes is, therefore, not a requirement for functionality with this invention. In addition, significant advantages may be seen over microplate ELISA formats due to increased binding capacity and steric flexibility.

Anticardiolipin antibodies (aCL) or antiphospholipid antibodies (aPL) are often found in sera from patients with primary antiphospholipid syndrome (PAPS), systemic lupus erythromatosis (SLE), HIV, and syphilis. Antiphospholipid antibodies appear to be directed to phospholipids in plasma membranes (See McNeil, et al., "Immunology and Clinical Importance of Antiphospholipid Antibodies" in *Advances in Immunology*, 49: 193–281, 1991). In patients with PAPS and SLE, antiphospholipid antibodies are associated with recurrent thrombosis, spontaneous abortion, and thrombocytopenia. Thus, monitoring for the presence of these antibodies is of diagnostic value. Current methods to detect these antibodies include radioimmunoassays, semi-automated microplate ELISA (enzyme linked immunosorbent assays) assays and coagulation type assays (see for example, WO 90/07368 to Barta et al.). Each method used for detection of antibodies to negatively charged phospholipids has some identified limitations. Coagulation assays used for detecting the presence of antiphospholipid antibodies in a test sample are labor intensive with test results based on subjective interpretation. Further, such assays are not typically automated and therefore not suited for use in screening large numbers of specimens.

There are also limitations associated with the detection of antiphospholipid antibodies in ELISA-type microplate assays. Typically, these assays involve the adsorption of cardiolipin (diphosphatidylglycerol) or other anionic phospholipids onto commercially available polystyrene microtiter plates. Such microplate assays are better than the coagulation tests for screening large numbers of specimens and provide for semiquantitative results. However, these microplate ELISA assays are not as specific or as sensitive as some of the coagulation tests. For example, it has been noted that some samples tested by such microplate formats exhibit binding lower than predicted when linear dilutions of sample are tested. The explanation for this is unclear.

It also has been observed that microplate ELISA assays for antiphospholipid antibodies do not perform satisfactorily in the presence of detergents such as NP-40 (Nonidet P-40) or Tween 20 (polyoxyethylene (20) sorbitan monolaurate). The use of detergents in microplate ELISA assays is generally believed to reduce non-specific binding of proteins or other reagent components to the solid phase and, thus, enhance the sensitivity and specificity of the assay. Tests performed using the microplate ELISA format may, therefore, show increased levels of false positive results related to non-specific binding in the absence of detergent. Therefore, it would be desirable to have a method of determining the presence or amount of antiphospholipid antibodies in a sample where either the use of detergents is not necessary or if used do not significantly affect the performance of the assay. Accordingly, this invention offers an improvement in this aspect also because the assay may be performed in the presence of detergents including FC100.

Yet another problem with microplate ELISA assays for antiphospholipid antibodies is that these assays require the physical attachment of the ligand directly to a solid phase. As discussed above, direct coupling may increase the risk of reduced sensitivity in these assays due to the steric hindrance imposed on the ligand and/or analyte that may prevent these molecules from reacting efficiently.

In contrast, the present invention provides a means of binding analyte to a solid phase through the use of the liposome reagent, which may result in reduction of problems associated with steric hindrance. It may also maximize the efficiency of ligand and analyte recognition and increase the total ligand binding capacity of the solid phase. The invention combines these features and also provides compositions and methods readily adaptable for a fully automated system.

SUMMARY OF THE INVENTION

The present invention provides methods for determining the presence or amount of analyte in a test sample comprising: contacting a liposome reagent comprising a liposome, a ligand chosen to bind specifically with the analyte and associated with the liposome membrane, and a haptenated component associated with the membrane of the liposome and where the hapten is chosen to bind specifically to a receptor immobilized on a solid phase, with test sample and the solid phase, simultaneously or sequentially for a time and under conditions sufficient for the analyte in the sample to bind to ligand in the liposome reagent and for the liposome reagent to bind to the receptor on the solid phase and detecting the presence or amount of analyte bound to the solid phase.

In another embodiment the invention provides a method for determining the presence or amount of antiphospholipid antibodies in a test sample wherein the ligand, an anionic phospholipid, preferably cardiolipin, that binds specifically to such antibodies, is incorporated into the membrane of the liposome and the haptenated component is also a phospholipid to which hapten is bound, which may be the same phospholipid as the ligand or it may be another anionic, neutral, or zwitterionic phospholipid.

Another embodiment of the invention relates to methods of determining or detecting an analyte in a test sample employing a liposome reagent comprising a liposome; a ligand chosen to bind specifically to the analyte and associated with the membrane of the liposome; and a haptenated component associated with the membrane of the liposome. The method comprises contacting test sample with a solid phase to which a receptor for analyte is bound to capture analyte onto the solid phase and simultaneously or sequentially adding the liposome reagent. The solid phase is then separated from the solution and contacted with a labeled receptor for the hapten. The amount of analyte bound to the solid phase via the liposome reagent is determined by determining the amount of label bound.

Yet another embodiment of the invention relates to a liposome reagent for use in an assay to detect analyte in a test sample comprising a liposome; a ligand chosen to bind specifically to the analyte and associated with the membrane of the liposome; and a haptenated component associated with the membrane of the liposome and where the hapten is chosen to bind specifically to a receptor on a solid phase used in the assay; and where the liposome is prepared so that during the assay the ligand and haptenated component remain associated with a portion of the membrane to maintain a linkage between the solid phase and ligand.

The invention also relates to a test kit for use in detecting the presence of analyte in a test sample which test kit includes a liposome reagent of the invention and a solid phase on which a receptor for the hapten of the liposome reagent is immobilized.

DETAILED DESCRIPTION OF THE INVENTION

Liposome reagents and methods for their use are detailed throughout this disclosure. The reagent preferably employs negatively charged phospholipids to form liposomes and may have various molecules intercalated or associated with the phospholipid membrane, depending on the intended use. As referred to herein "associated with" with respect to the liposome membrane means that a stable interaction between molecules was formed and maintained by covalent or non-covalent means and includes molecules intercalated or incorporated in the liposome membrane. A variety of applications for this assay are contemplated, including, but not limited to, a reagent for antiphospholipid antibody assay.

The following definitions are used throughout:

"Antiphospholipid antibodies" refers to antibodies that generally bind to negatively charged phospholipids, including cardiolipin (diphosphatidylglycerol), phosphatidylserine, phosphatidylinositol, and phosphatidic acid.

"Analyte" is used herein to refer to the compound or composition to be measured, preferably from a patient sample. The analyte is one member of a specific binding pair. In the preferred embodiment the other member of the specific binding pair is ligand. Analytes useful with the assays of this invention include antibodies, proteins, antigens, nucleic acids, steroids, and other substances having specific binding affinity for ligand and include preferably antiphospholipid antibodies.

"Ligand" is used herein to refer to a compound, molecule or the portion of the molecule that is a member of a specific binding pair, the other member of which is analyte or a receptor to which analyte binds. Ligand is chosen to specifically bind to analyte or the analyte receptor so that the amount of analyte bound to the ligand or analyte receptor during an assay is related to the amount of analyte present in a test sample. Ligand also includes ligand analogs where the ligand molecule is modified such that the portion of the molecule that specifically binds analyte or analyte receptor is removed from the native molecule through chemical, enzymatic or molecular manipulations and is affixed or associated with another molecule. Ligands are generally the smaller of the two components of the specific binding pair, however, this is not necessarily so. The ligand has one or more epitopes, may be antigenic or haptenated, and may be one or a group of compositions sharing at least one epitopic site. Illustrative ligands include autoantigens, allergens, anionic phospholipids, antibodies to tumor markers, and the like.

"Hapten" or "Haptenated" is used herein to refer to one member of a specific binding pair alone or attached to another compound or molecule where the other member is a receptor that is not analyte or ligand. Haptens are generally low molecular weight compounds capable of eliciting immune responses in laboratory animals usually when conjugated to a carrier, such as biotin, dinitrophenyl groups (DNP), fluorescein or its derivatives such as fluorescein isothiocyanate (FITC), digoxigenin and the like.

"Receptor" is used herein to refer to any compound or composition having specific binding affinity for hapten, haptenated compounds, ligand or analyte. Receptors useful with assays of the invention include antibodies, such as anti-biotin and anti-digoxigenin antibodies or anti-analyte antibodies, and other binding substances such as avidin, streptavidin, lectins, enzymes, intrinsic factor, folate binding protein, and the like. "Analyte receptor" is used herein to refer to a receptor having specific binding affinity for the analyte. "Hapten receptor" is used herein to refer to a receptor having specific binding affinity for the hapten or haptenated moiety.

"Label" or "labeled" is used herein to refer to a compound that is either directly or indirectly involved with the production of a detectable signal as a part of a signal detection system and is bonded directly to one or more molecule of a component of the assay. Label may be conjugated to carriers that specifically bind to analyte or ligand or may be incorporated into or associated with the membrane of a liposome reagent. Illustrative examples of labels include any of those known in the art, including enzymes, pigments, dyes, fluorophores, radioisotopes, stable free radicals luminescers such as chemiluminescers, biolumiescers, and the like. The term "detector" refers to any compound associated with a label. In a preferred signal detection system the label is an enzyme the detectable signal may be generated by exposing the labeled reagent to a particular substrate and incubating for color, fluorescence or luminescence development.

"Liposome" is used herein to refer to small discrete particles capable of maintaining their basic structural integrity in an aqueous environment and are formed from amphipathic molecules that have their hydrophilic surfaces exposed to surrounding aqueous medium, as well as hydrophilic surfaces exposed to an inner aqueous space. The membrane of the liposome shall be referred to as "membrane bilayer," "bilayer" or "membrane" interchangeably. Liposomes can be further classified, for example, as MLVs (MultiLamellar Vesicles), which are comprised of multiple concentric layers of lipid.

"Kit" is used herein to refer to a combination of reagents usually formulated with necessary buffers, salts, and stabilizers, where the reagents are premeasured so as to at least substantially optimize the assay sensitivity.

The term "protein" is used to herein to include molecules with protein components, polypeptide and peptide fragments.

The term "simultaneously" as used herein means that the assay components such as the liposome reagent, test sample or solid phase are each added to a reaction vessel at the same time or one immediately after the other so that all the assay components are combined in a reaction mixture. The term "sequentially" as used herein means that one assay component such as the liposome reagent is contacted with another assay component such as the test sample and/or solid phase for a time sufficient for a reaction to occur before one or all of the other assay components are added to the reaction mixture.

In one embodiment of this invention antiphospholipid antibodies are detected in immunoassays employing liposome reagents. Such antiphospholipid antibodies (aPL) are auto antibodies found in the plasma or serum of patients with PAPS (Primary Antiphospholipid Syndrome), in a subset of patients with systemic lupus erythematosus (SLE), in patients with certain infectious diseases, and may be drug induced in some cases. Antiphospholipid antibodies bind to cardiolipin or other negatively charged lipids. Thus, in a preferred aspect of this invention the assay employs liposome reagents comprising cardiolipin. Other negatively charged lipids that can also be used to detect antiphospholipid antibodies include phosphatidylserine, phosphatidylinositol, phosphatidic acid and the like. Other phospholipids that may be used to constitute the liposomal support (in combination with anionic phospholipids representing the ligand) include phosphatidylethanolamine, phosphatidylcholine, sphingomyelin, and the like.

As a first step for practicing the assays of this invention and detecting antiphospholipid antibodies in a test sample, liposomes are prepared that comprise one or more of the negatively charged phospholipids provided above. The negatively charged phospholipid cardiolipin is desirably combined with other phospholipids to create liposomes. Preferably, the liposomes comprise an unmodified phospholipid functioning as a ligand and a haptenated moiety to facilitate separation of the liposomes having analyte bound thereto during the assay process. The haptenated moiety is preferably haptenated lipid.

Haptenated lipids refer to lipids suitable for forming liposomes that have hapten attached in the hydrophilic portion. These haptenated lipids include lipids covalently linked to biotin, avidin, digoxigenin, DNP or the like. The hapten is desirably a low molecular weight compound, such as biotin, that can be readily attached to a lipid. Haptenated lipids useful with this invention can be purchased commercially, such as biotinylated dipalmitoylphosphatidylethanolamine (DPPE) available from Pierce Chemicals, Rockford, Ill., or can be manufactured using the methods disclosed by Rivnay, et al., "Use of Avidin-Biotin Technology for Liposome Targeting," in *Methods in Enzymology*, Vol. 149, pgs. 119–123 (1987).

Briefly, the phospholipid is dissolved in a solution of chloroform-methanol containing biotinyl N-hydroxysuccinimide ester (BNHS), followed by the addition of a chloroform solution containing 15% (v/v) triethylamine. The reaction proceeds for about two hours at room temperature and then the mixture is stored at about $-70°$ C. Purification is performed using gradient high-performance liquid chromatography. The column is first washed with a solvent mixture containing n-hexane/2-propanol/water (60:80:14, v/v/v) until a steady baseline is established followed by the introduction of a different solvent mixture containing n-hexane/2-propanol/water (60:80:7, v/v/v) until a new baseline of about 0.07 optical density (OD) units above the first baseline is established. Then the lipid sample is applied and the elution monitored with a M-441 discretewavelength ultraviolet detector (214 nm). The column is then eluted with the solvent solutions described above, 5 minutes with the second solution followed by a 20-minute linear gradient between 0 and 100% of the first solvent solution in the second. Then further elution in the first solvent for 45–70 minutes to achieve a stable baseline is performed. The peaks are collected, the eluted material pooled, and the solvent evaporated under a stream of nitrogen.

In a preferred embodiment of this invention the unmodified negatively charged phospholipid ligands include cardiolipin and the haptenated lipids include biotinylated DPPE. Other contemplated combinations include phosphatidylserine with biotinylated DPPE or phosphatidylinositol with biotinylated DPPE. However, any anionic phospholipid ligand to which antiphospholipid antibodies bind can be used in combination with any of the other phospholipids (which may be haptenated), including other anionic phospholipids, neutral and zwitterionic phospholipids.

Once the appropriate phospholipid ligand has been incorporated into or associated with liposomes having a biotinylated moiety, the liposome reagent can be used in an assay to detect antiphospholipid antibodies. Analyte present in a patient sample binds to the ligand incorporated into the liposomes and is captured by a solid phase via the haptenated lipid. In a preferred embodiment of the invention magnetically attractable particles conjugated to anti-biotin antibodies are used to capture the biotinylated phospholipid associated with the target ligand phospholipids. In a preferred version of the assay, biotinylated (bt-) DPPE was used to mediate capture of a mixed cardiolipin/bt-DPPE liposome reagents.

The liposome reagents of this invention may be formed by a variety of methods known in the art. For example, the present methods employ a modification of the methods described by Szoka, et al. (*Ann. Rev. Biophys. Bioeng.* 9:467–508, 1980) and Plant et al. (*Analyt. Biochem.* 176: 420–426 (1989), the teachings of which are incorporated herein by reference. A preferred method for forming liposomes, as further shown in Example 1 of this specification, is a modification of the method described by D. Papahadjopoulos and F. Szoka, Jr., in U.S. Pat. No. 4,235,871. Briefly, this process comprises three steps: (a) preparation and mixing of a solution of lipid to be deposited in an organic solvent; (b) evaporation of the solution to dryness using a solid stream of nitrogen gas to produce a thin film of phospholipid on a glass vessel; and, (c) hydration and formation of liposomes by vortexing (or other mechanical means) in an appropriate buffer. The resulting structure of the membrane bilayer is such that the hydrophobic (non-polar) tails of the lipid orient inward while the hydrophilic (polar) heads orient outwards toward the aqueous phase. The liposome preparation may be further separated, as needed, by column chromatography as described in Loughrey, et al. *J. Immun. Meth.*, Vol. 132, pgs. 25–35 (1990), centrifugation and/or dialysis.

Other methods that may be used for liposome formation include those of Batzri and Korn (*BioChim. BioPhys. Acta*, 281:1015, 1973). In the latter, liposomes were prepared by injection of the lipids in an organic phase into an aqueous solution. Methods for producing liposomes with improved stability include the method described by Law, et al., in U.S. Pat. No. 5,094,785 to produce non-aggregating ligand-linked liposomes. Methods for producing liposomes having a consistent liposome size thereby improving the reproducibility of assay results and manufacturing are described in U.S. Pat. No. 5,017,501.

It is further contemplated that a variety of phospholipid-derived liposomes could be used in the practice of the diagnostic methods of this invention. For example, any of a variety of liposomal structures could be used including unilamellar (possessing a single membrane bilayer) or multilamellar (characterized by multiple membrane layers) structures.

It is expected that certain ratios of target ligand to haptenated phospholipid, preferably cardiolipin to biotinylated DPPE, function better than others in diagnostic immunoassays. Molar ratios of 1:2.5 to 1:100 (biotinylated DPPE:Cardiolipin) may be used with the assays of the invention, ratios of 1:5 to 1:20 were used in most of the examples. Example 2 is provided to demonstrate that a variety of ratios of target ligand to haptenated phospholipid will function in this invention and provides a testing regime useful to optimize a particular assay by identifying optimal lipid ratios. While these assays are directed toward the combination of cardiolipin and biotinylated DPPE, those skilled in the art of lipid chemistry will readily recognize that other ratios and other lipids could similarly be tested for optimal activity without undue experimentation.

Solid phases useful with the invention are well known in the art and refer to an insoluble material to which one component of the assay may be bound, and include the walls of test tubes or wells of a microtiter plate, polystyrene beads, magnetically attractable beads (e.g., paramagnetic particles), nitrocellulose strips, membranes, latex microparticles, and others and made of hydrocarbon polymers such as polystyrene and polypropylene, glass, metals, gels or other materials. The "solid phase" is not critical and can be selected by one skilled in the art. Desirably, the solid phase is a particulate solid phase wherein the particles are capable of being suspended during the reaction. The benefits of using particles as the solid phase to facilitate separation are well known and some of the benefits are set forth in U.S. Pat. 4,554,088. Preferably, the solid phase particles used in an assay of this invention are magnetically attractable particles such as those described in U.S. Pat. No. 4,554,088. This patent also describes the benefits provided by the use of magnetically attractable particles as the solid phase in assays. Magnetically attractable particles allow the separation step to be done through magnetic separation and thus avoids the necessity of centrifuging or waiting for the particles to settle out of solution.

In the context of this invention, the terms "bound to" or "immobilized" encompasses all mechanism for binding antibodies and proteins, such as the receptor of the hapten/receptor pair of the invention, directly or indirectly to the solid phase so that during the performance of the assay the antibody or protein remains associated with the solid phase. Such mechanisms include covalent binding, non-covalent binding, chemical coupling, absorption by hydrophobic/hydrophobic, hydrophilic/hydrophilic or ionic interactions and the like.

In a preferred embodiment, the hapten receptor comprises goat antibiotin antibodies indirectly bound to the solid phase by burro anti-goat antibodies absorb onto the solid phase.

Ligand can be obtained from a variety of sources and is selected based on its ability to bind to analyte in a patient sample. When the analyte is antiphospholipid antibodies, cardiolipin is a preferred ligand and is commercially available.

Once the ligand-incorporating or ligand-associated liposomes have been prepared, it is useful to test the liposomes to ensure that the ligand is specific for the test analyte. Ligand specificity for test analyte can be determined in a number of ways.

For example, competitive assays can be used to demonstrate specificity of ligand-analyte binding. In such an assay a sample known to contain antiphospholipid antibodies is contacted with unhaptenated liposomes with incorporated or associated ligand, then with haptenated liposomes with incorporated or associated ligand. If the ligand is specifically binding with the analyte, the unhaptenated and haptenated liposomes will compete for binding to the same site on the analyte resulting in a reduction of signal detected relative to the assay control reaction performed with no unhaptenated ligand added.

Alternately, Example 3 of this specification details another method for determining the specificity of the liposome reagent for the test analyte. As shown in Example 3, various liposome preparations may be prepared using increasing concentrations of ligand, such as cardiolipin. Test sera containing antiphospholipid antibodies are tested with each liposome preparation. The amount of reactivity is then plotted as a function of ligand concentration employed in the liposome preparation. A linearity of dose with increasing amounts of ligand is used to demonstrate ligand specificity.

In one embodiment of the assay of invention, the liposome reagent incorporating a ligand such as cardiolipin and a haptenated moiety such as biotinylated DPPE is used in a heterogeneous assay wherein the solid phase includes an immobilized receptor for the hapten. Sample suspected of containing analyte is contacted with the liposome reagent and solid phase for a time and under suitable conditions for analyte present in the sample to complex to ligand incorporated into the liposome and for the liposome reagent-analyte complex to bind to the solid phase through the hapten/receptor interaction. The solid phase with bound analyte is then separated from the sample, washed and then contacted with a labeled specific binder for the analyte for a time and under conditions suitable to allow the labeled binder to bind to the bound analyte. The amount of bound label is then measured and related to the amount of analyte that was present in the sample. Generally, the amount of label detected in a sample is related to the amount of analyte in the sample by comparing the signal obtained with samples containing known concentrations of analyte with the signal obtained with the patient sample.

In another embodiment of the invention, the liposome reagent may be complexed with the solid phase having immobilized receptor through the hapten/receptor interaction before the solid phase is contacted with sample. In a preferred assay format, the assay employs magnetically attractable particles carrying immobilized antibiotin antibodies as the solid phase. The liposome reagent is then linked to the particles via its haptenated moiety, such as a biotinylated phospholipid.

In yet another embodiment of the assay of this invention, the liposome reagent further comprises a label compound, such as an enzyme, and preferably alkaline phosphatase, wherein the label compound is incorporated into or associated with the liposome membrane. In this embodiment, the liposome reagent is mixed with test sample suspected of containing analyte simultaneously or sequentially with a solid phase bearing hapten receptor. As above, after the analyte binds to the ligand of the liposome reagent which in turn is bound to the solid phase via the hapten/hapten receptor interaction, the bound analyte is separated from the unbound materials in the sample and the amount of label detected.

In yet another embodiment, the liposome reagent may be used to detect analyte that has been captured by the solid phase via a specific reaction. The analyte is desirably bound to an immobilized binding pair member chosen to bind the analyte at a site different from the ligand binding site, and preferably at a site sufficiently physically separated from the ligand binding site to minimize steric hindrance. In one embodiment, cardiolipin is the ligand and the analyte being detected is antiphospholipid antibodies. Anti-human antibodies (which bind to the Fc portion of the antiphospholipid antibodies) are immobilized on the solid phase. Then patient sample suspected of containing antiphospholipid antibodies is contacted with the solid phase simultaneously or sequentially with the liposome reagent for a time and under conditions suitable to allow all antibodies present in the sample to bind to the solid phase and for the liposome reagent to bind specifically with any antiphospholipid antibodies bound. After the bound liposome reagent is separated from unbound materials in the sample, a solution containing a predetermined amount of labeled receptor for the hapten is contacted with the solid phase and the amount of bound liposome reagent determined which amount is related to the amount of analyte in the sample.

In another embodiment of the assay of the invention to determine the amount or presence of antiphospholipid antibodies in a sample, a cofactor (believed by some in the field to be important for antiphospholipid antibody/phospholipid interaction) is included in the assay. In one embodiment, the cofactor may be intercalated into the liposome reagent of the invention along with the ligand and haptenated phospholipid, or haptenated and intercalated into the liposome reagents.

U.S. Pat. No. 5,344,758 to Krilis et al. teaches that antiphospholipid antibody binding to negatively charged phospholipid is enhanced in the presence of a purified co-factor that has been identified as beta-2-glycoprotein-I ($\beta$-2GPI). Their findings indicate that the presence of beta-2GPI, or an analog thereof is important for antibody phospholipid interaction, suggesting bound beta-2GPI forms the antigen to which antiphospholipid antibodies are directed. It should be noted that this observation that the co-factor is required is the subject of intensive debate. $\beta$-2-glycoprotein-1 (in purified or nonpurified forms) may be included in the assay of this invention by incorporation into the liposome reagent or added to the assay mixture in an aqueous solution. $\beta$-2-glycoprotein-I may be purified from normal human plasma or serum by affinity chromatography or by ion exchange chromatography. Chromatographic methods for isolating the cofactor are detailed by Krilis, et al. in U.S. Pat. No. 5,344,758, beginning at column 10 and see beginning at column 13, Examples 4 and 5.

In a preferred embodiment employing the cofactor, a stock solution of the cofactor is added to serum samples to obtain a final cofactor concentration of 50 µg/ml in the diluted sample. The samples are assayed for antiphospholipid antibodies using the assay methods herein. It should be noted that the methods of Krilis et al. employ a microplate ELISA-type assay and the use of biotinylated liposome/vesicles according to the present invention would be expected to present the phospholipids/co-factor in a conformation quite different from that presented when the phospholipids are directly coated onto a microplate.

As one aspect of this invention, the liposomes are used in an assay to detect the presence of antiphospholipid antibody in an automated assay format. In the examples, an automated analyzer generally as described in PCT Application No. PCT/US93/04209, published as International Publication No. WO 93/22686. Such an analyzer is commercially available from Sanofi Diagnostics Pasteur, Inc. USA under the trademark ACCESS. Any operational details not set forth below can be readily ascertained from this commercially available analyzer and/or its associated manuals.

There are significant benefits to using the liposome reagents to detect analyte present in serum or test samples at low concentrations. For example, since the liposome reagent has multiple binding sites there is increased capacity to recognize analyte within the assay. Additionally, a prevalent problem associated with antiphospholipid antibody assays is the heterogeneity of ligand presentation. Binding of the ligand to the solid phase using the liposome reagent of this invention is expected to improve the reproducibility of presentation of phospholipid ligands, like cardiolipin, over other assays employing phospholipid ligand affixed directly to a solid surface.

Additionally, the liposome reagents of this invention are more likely to present native ligand structure than are current microplate formats. Further, the epitopes would likely be more accessible to the antibody resulting in enhanced assay sensitivity as compared with assays where the negatively charged phospholipid is locked into a particular conformation such as would be found in solid phase assays for antiphospholipid antibodies.

Furthermore, instability of liposome preparations over time can be a problem with previously described liposome-based assay formats. We have found that the liposomes of this invention remain functional for use in assay formats of this invention when stored under nitrogen at 40° C. for greater than sixteen months making these preparations particularly suitable for use in assay kits.

References discussed herein are hereby expressly incorporated by reference into this text. Particular embodiments of this invention will be discussed in detail below and reference has been made to possible variations within the scope of the invention throughout this document. There are a variety of alternative techniques and procedures available to those skilled in the art that would similarly permit one to successfully practice the claimed invention without undue experimentation.

EXAMPLE 1

Preparation of Liposomes

In this example, liposomes were prepared using a mixture of the phospholipids, cardiolipin (also the ligand in these examples) and biotinylated dipalmitoylphosphatidylethanolamine (bt-DPPE, Pierce Chemicals, Rockford, Ill.).

To prepare a stock preparation of liposomes, a 0.2 ml–0.5 ml volume of ethanol containing 1 µmole (total) of phospholipid at a molar ratio approximately 1:20 bt-DPPE:CL (mixed by vortexing) was dried onto 12×75 mm glass tubes under a stream of nitrogen or argon gas, preferably for one half hour beyond evaporation of visible solvent. If the total phospholipid solution was not sufficient to cover the bottom of the tube (≦0.3 ml), additional ethanol was added before drying. Tubes having dried phospholipid film were stored in a dessicator under argon or nitrogen or under vacuum at ambient temperature for periods of up to several weeks until the films were hydrated to form liposomes. Lipid films stored under these conditions showed no observable decrease in the functionality of the liposome reagents.

To prepare liposomes, the lipid films prepared as above were hydrated by adding phosphate buffered saline (PBS, pH 7.2–7.4) to an appropriate hydration volume, and vortexing vigorously for about a minute. Other buffers used in this hydration step include Tris-buffered saline (TBS, pH 7.4) and PBS with 1% protein, either bovine serum albumin (BSA) or human serum albumin (HSA). When the phospholipid concentration in the hydration solution was sufficiently high (e.g., 1 mg/ml from input lipid solids) the solution was visibly cloudy. After vortexing the liposome preparation, it was incubated for 30–60 minutes by shaking in an orbital type shaker to increase liposome yield. This step may also produce more uniformly sized liposomes in the preparation.

Unincorporated molecules were separated from the liposome preparations using three methods. In these examples, the liposome preparations were micro-centrifuged at approximately 13,000×g, washed with PBS and the pellet fraction was isolated for use.

Another method of separating unincorporated molecules from the liposomes included chromatographing on a Sephacryl 300 column (Pharmacia) and equilibrating with PBS. In this method, the liposomes should be in the void volume and/or in the first few fractions. Therefore, these fractions were used for further study. In yet a third method, hydrated liposome preparations were dialyzed in PBS using tubing with a 50,000 dalton relative molecular weight cutoff.

When the liposome preparations were centrifuged reactivity toward samples with antiphospholipid antibodies was found in both the supernatant and the pellet of liposomes, indicating that liposomes or fragments thereof in which cardiolipin was incorporated were present in both. The pellet was assumed to contain liposomes only and, therefore, pellet fractions were used in most of these examples, except where noted as supernatant.

Liposomes prepared as described in this example were stable (with respect to retention of reactivity with samples with antiphospholipid antibodies) under nitrogen at 4° C. for more than sixteen months when stored in microfuge or screw-capped plastic tubes.

EXAMPLE 2

Characterization of Liposome Reagent
A. Effect of Variations in the Molar Ratio of Haptenated Phospholipids to Ligand Phospholipids To examine the effect of varying the molar ratios of bt-DPPE to cardiolipin on incorporation of the biotinylated component, a forty-fold variation in the starting phospholipid ratio was studied. Cardiolipin-containing liposomes were prepared by mixing a solution of cardiolipin (5 mg/ml cardiolipin in ethanol, Sigma, St. Louis, Miss. USA) with a solution of bt-DPPE (1 or 5 mg/ml in a 2:1 mixture of chloroform to methanol, LC form of bt-DPPE, from Pierce, Rockford, Ill., Cat No. 22010). Liposome preparations were made having the following bt-DPPE:CL ratios: 1:100, 1:50, 1:25, 1:10, 1:5 and 1:2.5 by mixing a constant amount of cardiolipin (100 µg) with varying amounts of bt-DPPE from 0 µg to 40 µg. Ethanol was added to each preparation to a total volume of 200 µl, the preparations were vortexed and then dried onto tubes in films as described in Example 1. The lipid films were hydrated as described above and unincorporated molecules removed through centrifugation. The liposome-containing pellets were then resuspended in PBS to a concentration of 40 µg/ml of total phospholipids.

In order to determine whether varying the ratio of bt-DPPE to cardiolipin in the liposomes affected the ability of the liposome reagent to be bound by the solid phase (anti-biotin paramagnetic particles in this example), assays were performed using an avidin-alkaline phosphatase conjugate (avidin-ALP conjugate) bound to bt-DPPE incorporated into liposomes to the solid phase through the anti-biotin antibody-biotin interaction.

The assay components included the liposome reagent preparations having varying ratios of bt-DPPE and one preparation with cardiolipin only liposomes, anti-biotin paramagnetic particles, avidin-ALP conjugate in dilution buffer, wash buffer and a chemiluminescent substrate.

The paramagnetic particles used in these assays were obtained from Rhone Poulenc (Paris, France) and coated with goat anti-biotin antibodies as described below. The anti-biotin antibodies were polyclonal antibodies obtained by injecting a keyhole limpet hemocyanin (KLH)-biotin immunogen into a goat and then affinity purifying the desired antibodies using a biotinylated BSA column. The particles were washed in deionized water and 2-(N- morpholino) ethanesulfonic acid (MES) buffer and activated by incubating them for about 30 minutes with a solution of N-hydroxysulfosuccinimide (sulfo-NHS) and 1-ethyl-3-(3-dimethylaminopropyl)-carbodiimide hydrochloride (EDC). The activated particles were separated from unreacted components by applying a magnetic field and resuspended in MES buffer. Burro anti-goat antibodies were adsorbed onto the particles by incubating a mixture of particles and anti-goat antisera (obtained from Pel-Freez, Inc., Rogers, Ark., and affinity purified on goat IgG) at 100 µg/ml for about two hours.

The particles were then washed in a buffer (1M glycine, pH 6.0) followed by a series of washes, first with Tris buffer at pH 8, then glycine buffer at pH 2.5 and then Tris buffer at pH 8 again. The particles were then resuspended in a storage buffer (Tris buffer with 0.1 BSA, preservatives and salt). The particles with bound anti-goat antibodies were combined with goat anti-biotin antisera obtained as described above at a concentration of 15 µg/mg and incubated overnight at ambient temperature.

The avidin-ALP conjugate was obtained from CalBiochem/Behring Diagnostics (La Jolla, Calif., Cat. # 189732) and diluted to 0.25 µg/ml in dilution buffer pH 7.7. The dilution buffer used in these examples, included 0.1M Tris, 0.1BSA, 0.25 µ/ml mouse IgG, 1.0 mM $MgCl_2$, 0.1 mM $ZnCl_2$, 0.15M NaCl, 0.2% Tween 20, 0.1% ProClin (a preservative manufactured by Rohm and Haas), 0.1% $NaN_3$, and 7% (v/v) heat inactivated normal equine serum (NES).

The wash buffer used in these examples includes 20 mM Tris, 0.15M NaCl, 0.05% (active solids) FC100 (a fluoro-alkyl sulfonate surfactant, sodium salt, ionic detergent, commercially available from 3M, St. Paul, Minn.), and 0.1% ProClin.

The chemiluminescent substrate used in these assays was LumiPhos® brand dioxetane chemiluminescent substrate (LumiPhos® 530 is commercially available from Lumigen, Inc, Detroit, Mich. USA), a composition that reacts with alkaline phosphatase to produce a detectable chemiluminescent signal.

In this experiment 25 µl of each liposome preparation (20 µg/ml) was mixed with 50 µl of 1 mg/ml anti-biotin paramagnetic particles and the volume of the reaction mixture brought to about 250 µl with wash buffer and the mixture incubated for about 30 minutes at 37° C. The bound liposome reagent was then separated from unbound reaction components through a series of three separation and wash steps where the reaction vessel containing the paramagnetic particles was placed in a magnetic field and the particles were attracted to the sides of the vessel (magnetic separation step), the solution aspirated from the vessel and then the particles were resuspended in wash buffer. After the third wash and aspiration step, the particles were resuspended in a solution containing 100 µl of the avidin-ALP conjugate and 250 µl of wash buffer. The mixture was incubated for about 30 minutes at 37° C. and then the unbound conjugate was separated from the conjugate bound to the particles by magnetic separation and washing as described above. The particles were then mixed with 250 µl of the LumiPhos® 530 substrate and incubated for about 5 minutes and the luminescence of the mixture was measured using a luminometer and expressed as Relative Luminometer Units (RLUs).

As reflected in Table 1, liposomes having molar ratios of haptenated phospholipid to ligand (cardiolipin in this example) ranging from 1:2.5 to 1:100 bt-DPPE:CL were able to bind to the solid phase in sufficient quantities to produce a detectable chemiluminescent signal greater than background, and the S/N ratio increased as more bt-DPPE was incorporated into the liposomes. In Table 1, S/N stands for the signal-to-noise ratio. S/N in these examples was determined by subtracting the RLU value obtained with the control preparation (cardiolipin-only liposomes, no biotin present) from the RLU value obtained with the liposome reagent preparation used in the assay and dividing the result by the control preparation value |(bt-DPPE:CL RLU value−control RLU value)/control RLU value|. In these assays, an S/N ratio greater than 5 is considered positive (P) or significantly greater than background, an S/N ratio of between 2 and 5 is considered indeterminate or borderline (B) and an S/N ratio of less than 2 is considered negative (N).

TABLE 1

Bt-DPPE Titration Response With Avidin-ALP Conjugate

| Liposome Composition | BtDPPE:CL ratio | MEAN RLUs | S/N |
|---|---|---|---|
| CL only | n/a | 24,156 | 0 |
| bt-DPPE:CL | 1:100 | 648,818 | 26 |
| bt-DPPE:CL | 1:50 | 1,393,385 | 57 |
| bt-DPPE:CL | 1:25 | 1,844,640 | 75 |
| bt-DPPE:CL | 1:10 | 2,810,540 | 115 |
| bt-DPPE:CL | 1:5 | 3,737,520 | 154 |
| bt-DPPE:CL | 1:2.5 | 4,404,780 | 181 |

B. Effect of Varying Total Phospholipid Concentration During Hydration.

The liposome reagents of the invention were further examined by using a fixed amount of total phospholipid and one molar ratio of bt-DPPE to cardiolipin of 1:10 but using different resuspension volumes in order to determine whether the lipid concentration during hydration affected the efficiency of the binding of the liposome reagents to the solid phase. The liposome reagent preparations used in this example were prepared as described above but hydrated in varying amounts of PBS with 1% HSA: 400 µl (20 µg/ml total phospholipid), 200 µl (40 µg/ml total phospholipid), 80 µl (100 µg/ml total phospholipid), or 40 µl (200 µg/ml total phospholipid), respectively. The cardiolipin-only control was hydrated in 200 µl PBS with 1% HSA to a concentration of 40 µg/ml. Each of the liposome reagent preparations was assayed as described above. As shown in Table 2, within the range of total phospholipid concentrations tested, the hydration volume was not critical (within the range tested) for functionality of the liposome reagent in this assay.

TABLE 2

Effect of Varying Phospholipid Concentration on Liposome Reagent

| Liposome Phospholipid Concentration | BtDPPE:CL ratio | MEAN RLUs | S/N |
|---|---|---|---|
| CL only | n/a | 24,156 | 0 |
| bt-DPPE:CL, 20 µg/ml | 1:10 | 3,168,020 | 130 |
| bt-DPPE:CL, 40 µg/ml | 1:10 | 2,810,540 | 115 |
| bt-DPPE:CL, 100 µg/ml | 1:10 | 2,059,150 | 84 |
| bt-DPPE:CL, 200 µg/ml | 1:10 | 2,865,070 | 118 |

C. Effect of Variations in the Molar Ratio of Haptenated Phospholipids to Ligand Phospholipids on the Ability of Liposome Reagents on Recognition by Antiphospholipid Antibodies in a Test Sample.

In order to determine whether varying the ratio of bt-DPPE to cardiolipin in the liposomes affected the ability of the liposome reagent to react with antiphospholipid antibodies in a serum sample, assays were performed using liposome reagent preparations with varying ratios of bt-DPPE as well as one preparation with cardiolipin-only liposomes. The liposome preparations were combined with serum containing antiphospholipid antibodies (as determined using The Diastat Anti-Cardiolipin Kit from Shield Diagnostics Ltd., The Technology Park, Dundee DD1 1SW, UK and the Kallestad Anti-Cardiolipin Microplate EIA kit from Sanofi Diagnostics Pasteur, Inc., Chaska, Minn. 55318), anti-biotin paramagnetic particles as described above, alkaline-phosphatase labeled conjugate of monoclonal anti-human IgG (anti-human IgG-ALP, Fc specific, obtained from The Binding Site, San Diego, Calif.), diluted to 0.1 µg/ml in dilution buffer, wash buffer and the chemiluminescent substrate.

The assays were performed as described above with 2 µl equivalents of serum, 100 µl anti-biotin paramagnetic particles, and the liposome reagent preparation combined in the first step of the assay. Also, the anti-human IgG-ALP conjugate was used in place of the avidin-ALP conjugate used in the assays described above.

As shown in Table 3, liposomes having molar ratios of haptenated phospholipid to ligand (cardiolipin in this example) ranging from 1:2.5 to 1:100 bt-DPPE:CL were able to bind antiphospholipid antibodies in the serum sample in sufficient quantities to produce a detectable chemiluminescent signal greater than background. Further, little change in the S/N ratio was observed with the varying amounts of bt-DPPE used in the preparation of the liposomes indicating sufficient capture capacity at a 1:100 ratio.

TABLE 3

Bt-DPPE Titration with Serum and Anti-IgG-ALP Phosphatase

| Liposome Reagent Composition | BtDPPE: CL ratio | MEAN RLUs | S/N |
|---|---|---|---|
| CL only | n/a | 677,022 | 0 |
| bt-DPPE:CL | 1:100 | 8,651,140 | 12 |
| bt-DPPE:CL | 1:50 | 9,622,645 | 13 |
| bt-DPPE:CL | 1:25 | 8,853,780 | 12 |
| bt-DPPE:CL | 1:10 | 8,310,435 | 11 |
| bt-DPPE:CL | 1:5 | 8,600,020 | 12 |
| bt-DPPE:CL | 1:2.5 | 6,497,990 | 9 |

D. Effect of Variations in Total Phospholipid Concentration During Hydration on the Ability of Liposome Reagents to Bind to Antiphospholipid Antibodies.

The liposome reagents of the invention were further examined by using a fixed amount of total phospholipid and one molar ratio of bt-DPPE to cardiolipin of 1:10 but using different resuspension volumes to determine varying such volumes affect the usefulness of the liposome reagents in detecting antiphospholipid antibodies. The liposome reagent preparations used in this example were prepared as described above but hydrated in varying amounts of PBS with 1% HSA, 400 µl (20 µg/ml), 200 µl (40 µg/ml), 80 µl (100 µl/ml), and 40 µl (200 µl/ml), respectively. The cardiolipin only control was hydrated in 200 µl PBS with 1% HSA.

Each of the liposome reagent preparations was assayed as described above using 100 µl (2 µl equivalents) of diluted human serum sample and the anti-human IgG-ALP conjugate. As shown in Table 4, within the range of total phospholipid concentrations tested, the results indicated no significant change in recognition by antiphospholipid antibodies due to the starting phospholipid concentration.

TABLE 4

Effect of Varying Phospholipid Concentration on Liposome Reagent Recognition by Antiphospholipid Antibodies

| Liposome Phospholipid Concentration | BtDPPE: CL ratio | MEAN RLUs | S/N |
|---|---|---|---|
| CL only | n/a | 24,156 | 0 |
| bt-DPPE:CL, 20 µg/ml | 1:10 | 9,182,860 | 13 |
| bt-DPPE:CL, 40 µg/ml | 1:10 | 8,310,435 | 11 |
| bt-DPPE:CL, 100 µg/ml | 1:10 | 10,285,220 | 14 |
| bt-DPPE:CL, 200 µg/ml | 1:10 | 8,945,220 | 12 |

Those skilled in the art can readily optimize their assays using these methods for determining the effect of lipid ratios and concentration on the effectiveness of the test assay.

EXAMPLE 3

Effect of Increasing Ligand Concentration in Assay

Liposome reagent preparations were prepared essentially as in Example 1, see above. In this case, 300 µl of 5 mg/ml of ligand solution (cardiolipin solution (1.5 mg) and 300 µl of 1 mg/ml bt-DPPE (300 µg) for a 5:1 ratio were dried onto tubes. A stock solution of each preparation was obtained by hydrating with a total volume of 1.8 ml PBS. Ligand concentrations of 0–1 µg/test were analyzed with a cardiolipin positive control serum in an automated analyzer as follows: 100 µl of liposome reagent preparation, 100 µl of diluted serum sample (serum sample was either serum known to contain antiphospholipid antibodies or normal human serum), 50 µl of 1 µg/ml paramagnetic particles and 100 ul of equine anti-human IgG-ALP conjugate (0.6 µg/ml in PBS with human serum albumin 1%) were added to a reaction vessel one after the other (simultaneously) incubated for thirty minutes and then washed three times as described above in Example 2. LumiPhose® brand 530 dioxetane chemiluminescent substrate (250 µl) was added, and the luminescence of the sample measured. As seen in Table 5, increased binding of the antiphospholipid antibodies in serum was observed as the ligand concentration was increased.

TABLE 5

Ligand Titration with Sera

| Ligand Concentration (µg/ml) | MEAN | S/N |
|---|---|---|
| 0 | 196,034 | 0 |
| 0.25 | 2,128,345 | 9.86 |
| 0.5 | 4,066,795 | 19.7 |
| 1.0 | 7,696,555 | 38.3 |
| 1.5 | 9,890,825 | 49.5 |
| 2.0 | 12,135,000 | 60.9 |
| 5.0 | 17,695,300 | 89.3 |
| 10.0 | 21,466,300 | 109 |

EXAMPLE 4

Assays to Detect Antiphospholipid Antibodies

Liposomes incorporating cardiolipin as the ligand and bt-DPPE were prepared essentially as in Example 1. In this case 300 μl of 5 mg/ml cardiolipin solution, and 300 μl of 1 mg/ml bt-DPPE for a 5:1 ratio were dried onto tubes.

Preparations were hydrated with a total volume of 1.8 ml PBS, for a stock concentration of 1 mg/ml. The liposome reagent preparation was diluted 1/200 in PBS, and assays were performed as described in Example 2 using paramagnetic particles as the solid phase with various patient samples and an anti-IgG-ALP conjugate. The same patient samples were also used in assays performed with two different commercially available microplate kits used to detect antiphospholipid antibodies. The microplate kits were the Kallestad Anti-Cardiolipin Microplate EIA kit available from Sanofi Diagnostics Pasteur, Inc., Chaska, Minn. and the Diastat Total Anti-Cardiolipin Kit from Shield Diagnostics Ltd., The Technology Park, Dundee, Scotland.

Twelve samples were tested for the presence of antiphospholipid antibodies using the method of this invention (the solid phase was paramagnetic particles) and in accordance with the instructions provided with the microplate kits. As shown in Table 6, the results of the tests performed with each of the microplate kits differed from each other in six of the twelve samples. Of the six samples where the results obtained with both kits was the same, the results of the assay of the invention agreed with those results. No conclusions can be drawn for the six out of twelve samples where there was no microplate consensus. However, this example does show that the assay of the invention is useful in detecting antiphospholipid antibodies in a test sample.

TABLE 6

Liposome Reagent Assay and Two Microplate Kits

| Sample No. | Liposome Reagent Assay | Kit 1 Result | Kit 2 Result |
|---|---|---|---|
| Blank | n/a | n/a | n/a |
| 1 | P | P | B |
| 2 | P | P | P |
| 3 | N | N | P |
| 4 | P | P | P |
| 5 | P | P | P |
| 6 | P | P | P |
| 7 | P | P | P |
| 8 | N | N | P |
| 9 | N | N | P |
| 10 | N | P | B |
| 11 | N | N | P |
| 12 | N | P | P |

P-Positive Result
B-Borderline Result
N-Negative Result

EXAMPLE 5

Use of Haptenated Liposomal Ligand in a Microplate ELISA Format.

Liposomes incorporating cardiolipin and bt-DPPE were prepared essentially as in Example 1. In this case, the haptenated liposome reagent was bound by the analyte that was captured by an anti-human antibody (which binds to the Fc portion of the analyte antibodies) immobilized on the well of a microplate. In this case, the analyte/liposome reagent complex was detected using a conjugate comprising a receptor for the hapten and an alkaline phophatase label. Microplates (Nunc, Denmark #4–41653) were washed with deionized water and then coated with goat anti-human antibody (goat anti-human, anti-IgG, anti-IgM, Jackson Laboratories, Cat #109005127) as described below: Antibody was diluted to 1 mg/ml in 0.05M glycine/0.1M NaCl. pH 3, and incubated for 15 minutes at room temperature. The pH was neutralized by diluting the antibody solution in a 50 fold excess of 0.1M potassium phosphate, pH 7.4, for a final concentration of antibody of 20 μg/ml. 100 μl of the neutralized antibody solution was added to each well of washed plates and incubated overnight at 4° C. Then the plates were washed three times with PBS to remove unbound antibody, then incubated with PBS/1- BSA (Fraction V, Sigma Chemicals) for 60 minutes at 37° C.

Before use in the assays the plates were washed again. In the assays, 100 μl of patient sample (diluted 1:25 in PBS with 0.1% BSA) were added to appropriate wells and incubated for two hours at 37° C. A normal human serum control and an antiphospholipid antibody sera were included as negative and positive controls.

After the two hour incubation the plates were washed three times in PBS. The liposome reagent preparations prepared as in Example 2 but with CL:bt-DPPE ratios of 5:1 to 20:1 and a CL control with no bt-DPPE. 100 μl of each of the liposome preparations (1:25 and 1:100 dilutions of the original stock 1mg/ml liposome reagent preparation) and a negative control (with no ligand) were added to appropriate wells and incubated for 90 minutes at room temperature.

The plates were washed three times to remove excess liposome reagent and a streptavidin-alkaline phosphatase conjugate (Jackson #016050084, diluted 1/10,000 in PBS/0.1% BSA), was added and the plates incubated for 60 minutes at room temperature. Then the plates were washed and 100 μl of a p-nitrophenyl phosphate (PNPP) substrate was added. After a 30 minute incubation the reaction was stopped and the amount of signal generated measured spectrophotometrically at 405 nm.

The results indicated that the liposome reagent was captured by antiphospholipid antibodies in the test sample.

EXAMPLE 6

Liposomal Ligand with Label Associated With Membrane

In this example, liposome reagents were prepared having a phospholipid ligand incorporated into the liposome membrane, along with the haptenated phospholipid and a protein, in this case, a label compound, alkaline phosphatase.

Five different liposome preparations were made generally as described in Example 1. In the first dry down step of the method described in Example 1, 20 μl of the cardiolipin stock solution (5 mg/ml) was combined with no bt-DPPE and 180 μl of ethanol in tube 1. In tubes 2–5, 20 μl of the cardiolipin stock solution was combined with 5 μl of bt-DPPE stock solution (5 mg/ml) and 175 μl of ethanol. In the hydration step, an alkaline phosphatase solution, (Boehringer, West Germany, Cat.#556602), an alkaline phosphatase buffer (the same buffer used in the alkaline phosphatase solution about, but without the enzyme, 3M NaCl, 1 mM $MgCl_2$, 0.1 mM $ZnCl_2$, 30 mM triethanolamine, pH 7.6) and phosphate buffer (50 mM, pH 7.2) were added in varying amounts to tubes 1–5 having the phospholipid films dried thereon. 110 μl of ALP solution and 890 μl of phosphate buffer were added to tube 1. 110 pl of ALP buffer, and 890 μl of phosphate buffer were added to tube 2. 22 μl of ALP solution, 88 μl of ALP buffer, and 890 μl of phosphate buffer were added to tube 3. 55 μl of ALP solution, 55 μl of ALP buffer, and 890 μl of phosphate buffer were added to tube 4. 110 μl of ALP solution and 890 μl of phosphate buffer were added to tube 5.

The tubes were vortexed and incubated as described in Example 1. The tubes were then washed to remove unincorporated ALP. Then 1 ml PBS was added to each preparation, mixed, centrifuged in a microfuge and supernatant removed. This wash step was repeated two more times and then the liposomal pellet resuspended in 500 μl of PBS. In order to determine whether the alkaline phosphatase was incorporated/associated with the liposome reagents, 25 μl of each of the liposome preparations was mixed with 50 μl of anti-biotin paramagnetic particles and the volume of the reaction mixture brought to about 250 μl with wash buffer and the mixture incubated for about 30 minutes at 370° C. The bound liposome reagent was then separated from unbound reaction components through a series of separation and wash steps as described in Example 2. The particles were then mixed with 250 μl of the LumiPhos® 530 substrate and incubated for about 5 minutes and the luminescence of the mixture was measured using a luminometer and expressed as Relative Luminometer Units (RLUs). Generation of signal indicated incorporation/ association of the ALP into or with the liposome.

TABLE 7

Alkaline Phosphatase Associated with Liposomes

| Liposome Reagent Preparation | Tube 1<br>No bt-DPPE<br>CL/ALP<br>550 μg/ml ALP | | Tube 2<br>No ALP<br>CL/bt-DPPE | | Tube 3<br>100:1<br>CL/ALP<br>110 mg/ml ALP | | Tube 4<br>50:1<br>CL/ALP<br>220 μg/ml ALP | | Tube 5<br>20:1<br>CL/ALP<br>550 μg/ml | |
|---|---|---|---|---|---|---|---|---|---|---|
| Dilution | MEAN | S/N | MEAN | S/N | MEAN | S/N | MEAN | S/N | MEAN | S/N |
| 1/10 | 157,050 | 0 | 10,980 | −1 | 1,705,640 | 10 | 3,996,975 | 24 | 7,854,840 | 49 |
| 1/100 | 37,316 | 0 | 9,976 | −1 | 324,739 | 8 | 782,348 | 20 | 1,531,940 | 40 |
| 1/1000 | 10,175 | 0 | 9,261 | 0 | 45,834 | 4 | 97,220 | 9 | 213,132 | 20 |
| 1/10,000 | 9,441 | 0 | 9,439 | 0 | 12,442 | 0 | 15,931 | 1 | 18,797 | 1 |

As shown in Table 7 the results indicated that ALP was associated/intercalated into the liposome reagents and the liposome reagents were functional after rudimentary separation by microfuging to remove unincorporated ALP. The S/N ratio was still increasing at the highest concentration of ALP used in the liposome preparation step indicating that additional ALP could be added to increase the S/N ratio if desired. In this example, the S/N ratio was determined as follows: |(Mean Value obtained with Liposome Reagent-Mean Value obtained with Liposome Reagent of same dilution in Tube 1)/Mean Value of Tube 1|.

While particular embodiments of the invention have been described in detail, it will be apparent to those skilled in the art that these embodiments are exemplary rather than limiting, and the true scope of the invention is that defined in the following claims.

What is claimed is:

1. A liposome reagent for use in an assay to detect analyte in a test sample comprising:
   a liposome having a membrane;
   a ligand chosen to bind specifically to the analyte and associated with the membrane of the liposome; and
   a haptenated component associated with the membrane of the liposome and where the hapten is chosen to bind specifically to either a hapten receptor on a solid phase or to a hapten receptor on a label compound that is a component of a signal detection system used in the assay;
   and where the liposome is prepared so that during the assay the ligand and haptenated component remain associated with a portion of the membrane so that a linkage between the solid phase and ligand is maintained.

2. The reagent of claim 1 wherein the ligand is a phospholipid.

3. The reagent of claim 1 wherein the ligand is an anionic phospholipid.

4. The reagent of claim 1 wherein the analyte is an antiphospholipid antibody.

5. A method for determining the presence or amount of analyte in a test sample employing a liposome reagent comprising a liposome having a membrane, a ligand chosen to bind specifically with the analyte and associated with the liposome membrane, and a haptenated component associated with the liposome membrane and where the hapten is chosen to bind specifically to a hapten receptor on a solid phase of an assay, the method comprising:
   contacting the liposome reagent with test sample and the solid phase on which the hapten receptor is bound, simultaneously or sequentially for a time and under conditions sufficient for the analyte in the sample to bind to ligand in the liposome reagent and for the haptenated liposome reagent to bind to the receptor on the solid phase, forming an analyte-ligand complex linked to a hapten-hapten receptor complex through a portion of the liposome membrane; and
   detecting the presence or amount of analyte-ligand complex bound to the solid phase.

6. The method of claim 5 further comprising determining the amount or presence of analyte by contacting the solid phase to which analyte in the test sample is bound with a predetermined amount of a labeled reagent that will specifically bind to the analyte and detecting the label.

7. The method of claim 6 wherein the label is selected from the group consisting of enzymes, radioisotopes, stable free radicals, chemiluminescent compounds, bioluminescent compounds, fluorescent compounds, dyes and enzyme substrates.

8. The method of claim 7 wherein the label is an enzyme.

9. The method of claim 8 wherein the label is an enzyme selected from the group consisting of alkaline phosphatase and horseradish peroxidase.

10. The method of claim 5 wherein the solid phase is selected from the group consisting of walls of test tubes, wells of microtiter plates, particles, and nitrocellulose strips.

11. The method of claim 10 wherein the solid phase is a suspendable particle.

12. The method of claim 11 wherein the solid phase is a magnetically attractable particle.

13. A method for determining the presence or amount of antiphospholipid antibodies in a test sample employing a liposome reagent comprising a liposome having a membrane, a phospholipid ligand chosen to bind specifically with the antiphospholipid antibodies, and a haptenated component associated with the membrane of the liposome and where the hapten is chosen to bind specifically to a hapten receptor on a solid phase of an assay, the method comprising:

contacting the liposome reagent with the test sample and the solid phase carrying the hapten receptor, simultaneously or sequentially for a time and under conditions sufficient for the antiphospholipid antibodies in the sample to bind to the phospholipid ligand in the liposome reagent and for the haptenated liposome reagent to bind to the receptor on the solid phase; and detecting the presence or amount of analyte bound to the solid phase.

14. The method of claim 13 wherein the phospholipid ligand is an anionic phospholipid.

15. The method of claim 14 wherein the anionic phospholipid is selected from the group consisting of cardiolipin, phosphatidylinosityl, phosphatidylserine, and phosphatidic acid.

16. The method of claim 13 wherein the haptenated component is a haptenated phospholipid.

17. The method of claim 16 wherein the phospholipid that is haptenated is selected from the group consisting of cardiolipin, phosphatidylinosityl, phosphatidylserine, phosphatidylethanolamine, sphingomyelin and phosphatidic acid.

18. The method of claim 16 wherein the haptenated phospholipid is haptenated dipalmitoylphosphatidylethanolamine.

19. The method of claim 13 wherein the liposome reagent includes β-2-glycoprotein I associated with the membrane of the liposome.

20. The method of claim 13 further comprising the step of contacting the liposome reagent and test sample with a solution comprising β-2-glycoprotein I.

21. A kit for use in an assay to determine the presence or amount of analyte present in a test sample comprising:

a liposome having a membrane reagent comprising a liposome, a ligand chosen to bind specifically to the analyte and associated with the membrane of the liposome and a haptenated component associated with the membrane of the liposome and where the hapten is chosen to bind specifically to a hapten receptor bound to a solid phase and where the liposome is prepared so that during the assay the ligand and haptenated component remain associated with a portion of the membrane so that a linkage between the solid phase and ligand is maintained, and the solid phase.

22. A kit for use in an assay to determine the presence or amount of analyte present in a test sample comprising:

a liposome having a membrane reagent comprising a liposome, a ligand chosen to bind specifically to the analyte and associated with the membrane of the liposome and a haptenated component associated with the membrane of the liposome and where the hapten is chosen to bind specifically to a hapten receptor on a label compound that is an element of a signal detection system and where the liposome is prepared so that during the assay the ligand and haptenated component remain associated with a portion of the membrane so that a linkage between a solid phase and ligand is maintained, solid phase with receptor bound and label compound.

23. A liposome reagent for use in an assay to detect antiphospholipid antibodies in a test sample comprising:

a liposome having a membrane;

a phospholipid ligand chosen to bind specifically to the antiphospholipid antibodies and associated with the membrane of the liposome; and a haptenated component associated with the membrane of the liposome and where the hapten is chosen to bind specifically to a hapten receptor on a solid phase used in the assay; and where the liposome is prepared so that during the assay the phospholipid ligand and haptenated component remain associated with a portion of the membrane to maintain a linkage between the solid phase and phospholipid ligand.

24. The liposome reagent of claim 23 further including β-2-glycoprotein I associated with the membrane of the liposome.

* * * * *